United States Patent [19]

Coope et al.

[11] Patent Number: 5,753,599
[45] Date of Patent: May 19, 1998

[54] THIADIAZOLE DIOXIDES AS BLEACH ENHANCERS

[75] Inventors: Janet Lynn Coope, Hackensack; Mohamed Gaznabi Khan, Montclair, both of N.J.; Karl Friedrich Moschner, Troy, N.Y.

[73] Assignee: Lever Brothers Company, Division of Conopco, Inc., New York, N.Y.

[21] Appl. No.: 760,157

[22] Filed: Dec. 3, 1996

[51] Int. Cl.$^6$ .............................. C11D 7/18; A61K 7/30; D06L 3/02; D06L 3/16
[52] U.S. Cl. ................... 510/116; 510/226; 510/235; 510/295; 510/298; 510/305; 510/306; 510/310; 510/314; 510/372; 510/375; 510/378; 510/407; 252/186.26; 252/186.27; 252/186.31; 252/186.38; 252/186.39; 252/186.41; 252/186.42; 252/186.43; 8/110; 8/111; 8/137
[58] Field of Search .................... 510/116, 226, 510/235, 295, 298, 303, 304, 305, 306, 310, 314, 369, 371, 372, 374, 375, 378, 407; 252/186.26, 186.29, 186.31, 186.38, 186.39, 186.41, 186.42, 186.43; 8/137, 111, 110

[56] References Cited

U.S. PATENT DOCUMENTS

| | | |
|---|---|---|
| 3,115,496 | 12/1963 | Wright . |
| 3,186,998 | 6/1965 | Wright . |
| 3,518,170 | 6/1970 | Koretzky . |
| 5,041,232 | 8/1991 | Batal et al. . |
| 5,045,223 | 9/1991 | Batal et al. . |
| 5,047,163 | 9/1991 | Batal et al. . |
| 5,463,115 | 10/1995 | Batal et al. . |

OTHER PUBLICATIONS

J.B. Wright, J. Org. Chem., 29, pp. 1905–1909 (1964).

*Primary Examiner*—Margaret Einsmann
*Attorney, Agent, or Firm*—Milton L. Honig

[57] ABSTRACT

Novel bleaches, a method for bleaching substrates using these materials and detergent compositions containing same are reported. The bleaches are thiadiazole dioxides. Substrates such as fabrics may be bleached in an aqueous solution containing the thiadiazole and a peroxygen compound.

16 Claims, No Drawings

THIADIAZOLE DIOXIDES AS BLEACH ENHANCERS

BACKGROUND OF THE INVENTION

1. Field of the Invention

The invention relates to bleach catalysts, compositions containing same and a method for using the catalysts for cleaning substrates, especially fabrics.

2. The Related Art

Many household and personal care products are formulated with an active oxygen-releasing material to effect removal of stain and soil. Oxygen-releasing materials have an important limitation; their activity is extremely temperature dependent. Temperatures in excess of 60° C. are normally required to achieve any bleach effectiveness in an aqueous wash system. Especially for cleaning fabrics, high temperature operation is both economically and practically disadvantageous.

The art has partially solved the aforementioned problem through the use of activators. These activators, also known as bleach precursors, often appear in the form of carboxylic acid esters. In an aqueous liquor, anions of hydrogen peroxide react with the ester to generate the corresponding peroxyacid which oxidizes the stained substrate. Commercial application of this technology is found in certain fabric bleaching detergent powders incorporating sodium nonanoyloxybenzene sulfonate. This activator is typical of a class that features a phenol sulfonate leaving group; see U.S. Pat. No. 4,412,934 (Chung et al.).

While carboxylic acid ester activators and the like are often effective, they are not catalytic. Once the ester has been perhydrolyzed it can no longer be recycled. Accordingly, relatively large amounts of activator are necessary. Amounts as high as 8% may be necessary in a detergent formulation for bleaching fabrics. Cost for these relatively expensive activators is of major concern at such levels.

A significant advance in catalysis was reported utilizing sulfonimines in U.S. Pat. No. 5,041,232, U.S. Pat. No. 5,047,163, U.S. Pat. No. 5,045,223 and U.S. Pat. No. 5,463,115 all to Batal and Madison. Only a few of the reported compounds have been studied in any detail. More investigation needs to be conducted to identify catalysts of even greater activity.

Accordingly, it is an object of the present invention to provide novel bleach catalysts that can operate over a wide temperature range including that of under 60° C.

It is another object of the present invention to provide bleach catalysts which are effective at relatively low concentrations thereby achieving a cost effective stain removal system.

Still another object of the present invention is to provide bleach catalysts which have lower dye fading properties than previous catalysts.

A further object of the present invention is to provide a method for bleaching stained substrates such as clothes, household hard surfaces including sinks, toilets and the like, and even dentures.

Other objects of the present invention will become apparent through the following summary, detailed discussion and examples.

SUMMARY OF THE INVENTION

A bleaching composition is provided including:

(i) from 1 to 60% by weight of a peroxygen compound; and (ii) from 0.01 to 10% of an oxygen transfer agent whose structure is:

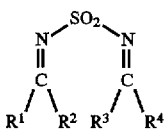

wherein:

$R^1$, $R^2$, $R^3$ and $R^4$ may each independently be hydrogen, nitro, halo or a $C_1$–$C_{40}$ substituted or unsubstituted radical selected from the group consisting of phenyl, aryl, acyl, heterocyclic ring, alkyl, cycloalkyl, cyano, alkoxy, keto, carboxylic and carboalkoxy radicals; and $R^1$ with $R^2$ or $R^2$ with $R^3$ or $R^3$ with $R^4$ or $R^1$ with $R^4$ may respectively independently form a ring system, and when $R^2$ and $R^3$ are absent, carbon atoms of the imine groups may directly be bonded together.

Additionally, there is provided a method for bleaching a stained substrate comprising the step of applying to the stained substrate an aqueous solution comprising a peroxygen compound and an oxygen transfer agent whose structure is $R^1R^2C=NSO_2N=CR^3R^4$, with radical groups as defined above, the mole ratio of peroxygen compound to oxygen transfer agent being from about 250:1 to about 1:2.

Certain novel compounds are also provided whose structure is $R^1R^2C=NSO_2N=CR^3R^4$ having radical groups as defined above, with the proviso that at least one of $R^1$, $R^2$, $R^3$ is substituted with a water-solubilizing functional group. Typical water-solubilizing groups include carboxylic acid, phosphoric acid, phosphonic acid, sulfuric acid, sulfonic acid, and, especially, their salt derivatives and quaternary ammonium salts.

DETAILED DESCRIPTION

It has been found that thiadiazole dioxides operate even more effectively than sulfonimines as catalysts for activating peroxygen compounds to transfer active oxygen to stains. Consumer and industrial articles can effectively be bleached to remove stains present on such articles. Thiadiazole dioxides covered by the present invention are those whose structure is:

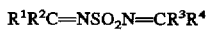

wherein:

$R^1$, $R^2$, $R^3$ and $R^4$ may each independently be hydrogen, nitro, halo or a $C_1$–$C_{40}$ substituted or unsubstituted radical selected from the group consisting of phenyl, aryl, acyl, heterocyclic ring, alkyl, cycloalkyl, cyano, alkoxy, keto, carboxylic and carboalkoxy radicals; and $R^1$ with $R^2$ or $R^2$ with $R^3$ or $R^3$ with $R^4$ or $R^1$ with $R^4$ may respectively independently form a ring system, and when $R^2$ and $R^3$ are absent, carbon atoms of the imine groups may directly be bonded together.

Often advantageous are thiadiazole dioxides having at least one of $R^1$, $R^2$, $R^3$, $R^4$ substituted with a water-solubilizing functional group. These functional groups may be selected from carboxylates, phosphates, phosphonates, sulfates, sulfonates in acid and salt form and quaternary ammonium salts. Suitable salts include those whose counterions are selected from alkali metal, ammonium, and $C_2$–$C_6$ alkanolammonium cations.

Amine functional groups may also be incorporated into $R^1$, $R^2$, $R^3$ or $R^4$ to provide water-solubilization of the thiadiazole dioxides. An example combining the amine and heterocyclic structure is that of pyridine.

A water-solubilizing functional group is one which renders the thiadiazoles soluble to the extent of at least 2 mg/l, preferably at least 25 mg/l, optimally at least 250 mg/l by weight in water at 25° C.

Heterocyclic rings according to this invention include cycloaliphatic and cycloaromatic type radicals incorporating an oxygen, sulfur and/or nitrogen atom within the ring system. Representative nitrogen heterocycles include pyridine, morpholine, pyrrole, imidazole, triazole, tetrazole, pyrrolidine, piperidine and piperazine. Suitable oxygen heterocycles include furan, tetrahydrofuran and dioxane. Sulfur heterocycles may include thiophene and tetrahydrothiophene. Among the various heterocycles, it has been found that those incorporating nitrogen are the most active.

The term "substituted" is defined in relation to $R^1$, $R^2$, $R^3$, $R^4$ as a substituent which is a nitro, halo, cyano, alkyl, acyl, amino, aminoalkyl, thioalkyl, sulfoxyalkyl, carboxyester, hydroxy, alkoxy, polyalkoxy and quaternary di- or trialkylammonium function, and wherein any carbon moiety has from 1 to 40 carbon atoms.

The most preferred embodiments of this invention are 3,4-substituted 1,2,5-thiadiazole 1,1-dioxides. Representative structures are described below wherein $R^1$ and $R^2$ are varied as follows:

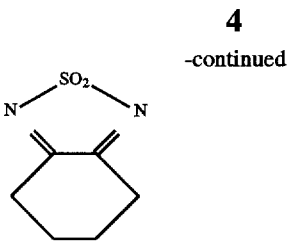

| COMPOUND | $R^1$ | $R^4$ |
|---|---|---|
| 1 | $CH_3$ | $CH_3$ |
| 2 | $CH_3$ | Phenyl |
| 3 | Phenyl | Phenyl |
| 4 | $CH_3CH_2$ | $CH_3CH_2$ |
| 5 | $CH_3(CH_2)_7$ | $CH_3$ |
| 6 | $CH_2N^+(CH_3)_3$ | $CH_3$ |
| 7 | $CO_2H$ | $CO_2H$ |
| 8 | $CH_2Br$ | $CH_2Br$ |
| 9 | $CH_2OH$ | $CH_2OH$ |
| 10 | $CH_3$ | $CH_2NO_2$ |
| 11 | $CO_2Me$ | $CO_2Me$ |
| 12 | 4-Cl-Phenyl | $CH_3$ |
| 13 | 2-Cl-Phenyl | $CH_3$ |
| 14 | 4-$(CH_3)_3N^+$-Phenyl | $CH_3$ |
| 15 | $CH_2CN$ | $CH_2CN$ |
| 16 | Phenyl | $CH_2CH_2CH_3$ |
| 17 | Phenyl | H |
| 18 | $CH_3$ | H |
| 19 | H | H |
| 20 | Phenyl | $CF_3$ |
| 21 | Pyridyl | Pyridyl |

Other representative structures include:

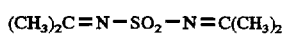 (22)

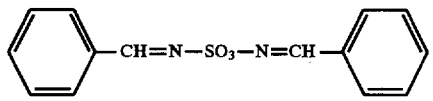 (23)

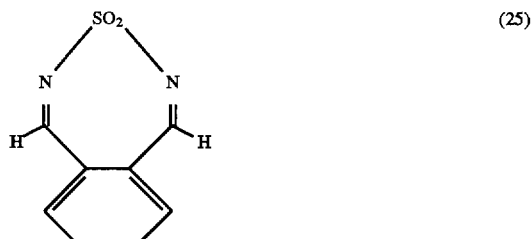 (24)

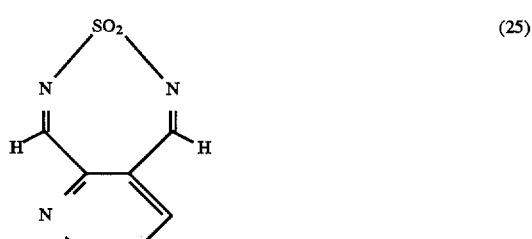 (25)

(25)

(27)

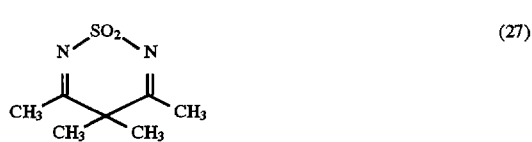

The foregoing oxygen transfer agents may be incorporated into detergent bleach compositions along with a further essential component which is a peroxygen compound capable of yielding peroxide anion or peroxyacid in an aqueous solution.

Amounts of oxygen transfer agent suitable for the present invention may range from 0.01 to 10%, preferably from 0.1 to 5%, optimally between 0.5 and 1.5% by weight of the composition.

The peroxygen compound may be present from 1 to 65%, preferably from 1.5 to 25%, optimally between about 2 and 10% by weight.

The molar ratio of peroxygen compound to oxygen transfer agent will range from about 250:1 to 1:2, preferably 100:1 to 1:1, optimally between about 25:1 to 2:1.

Peroxyacid and peroxide anion sources are well known in the art. They include the alkali metal peroxides, organic peroxides such as urea peroxide, and inorganic persalts, such as the alkali metal perborates, percarbonates, perphosphates, persilicates and persulfates (e.g. Oxone®). Mixtures of two or more such compounds may also be suitable. Particularly preferred are sodium percarbonate, Oxone® and sodium perborate monohydrate.

Alkylhydroperoxides are another suitable class of peroxygen compounds. Examples of these materials include cumene hydroperoxide and t-butyl hydroperoxide.

The organic peroxy acids usable in the present invention can contain either one or two peroxy groups and can be either aliphatic or aromatic. When the organic peroxy acid is aliphatic, the unsubstituted acid has the general formula:

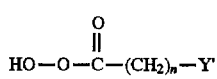

where Y' can be, for example, H, CH$_3$, CH$_2$Cl, COOH, NHCOOOH or COOOH; and n is an integer from 0 to 20.

When the organic peroxy acid is aromatic, the unsubstituted acid has the general formula:

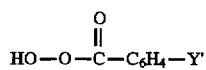

wherein Y' is hydrogen, alkyl, alkylhalogen, halogen, COOH, NHCOOOH or COOOH.

Typical monoperoxy acids useful herein include alkyl peroxy acids and aryl peroxy acids such as:

(i) peroxybenzoic acid and ring-substituted peroxybenzoic acids, e.g. peroxy-α-naphthoic acid;

(ii) aliphatic, substituted aliphatic and arylalkyl monoperoxy acids, e.g. peroxylauric acid, peroxystearic acid, and N,N-phthaloylaminoperoxycaproic acid (PAP).

Typical diperoxy acids useful herein include alkyl diperoxy acids and aryldiperoxy acids, such as:

(iii) 1,12-diperoxydodecanedioic acid;

(iv) 1,9-diperoxyazelaic acid;

(v) diperoxybrassylic acid; diperoxysebacic acid and diperoxyisophthalic acid;

(vi) 2-decyldiperoxybutane-1,4-dioic acid;

(vii) 4,4'-sulfonylbisperoxybenzoic acid;

(viii) N,N'-terephthaloyl-di(6-aminoperoxycaproic acid).

Particularly preferred organic peroxyacids are N,N-phthaloylaminoperoxycaproic acid, peracetic acid, monoperoxyphthalic acid (magnesium salt hexahydrate), and diperoxydodecanedioic acid. Under certain circumstances, hydrogen peroxide itself may directly be employed as the peroxygen compound.

Optionally, compositions of the present invention may further include a pre-bleach precursor that reacts with peroxide anion or peroxyacid and forms therewith a peracid, percarbonic acid or perimidic acid.

The preferred precursors are N,N,N',N'-tetraacetylethylene diamine (TAED), tetraacetyl-glycoluril (TAGU), glucose pentaacetate, xylose tetraacetate, sodium acetyloxybenzene sulfonate (SABS) and sodium nonanoyloxybenzene sulfonate (SNOBS). Levels of precursor may range from 0.1 to 40%, preferably from 1 to 10%, optimally from 2 to 8% by weight.

Compositions of the present invention may also include a transition metal catalyst. Suitable transition metals include ions selected from the group consisting of chromium, cobalt, titanium, nickel, iron, copper, molybdenum, vanadium, tungsten, palladium, platinum, lanthanum, rhenium, rhodium, ruthenium, manganese and mixtures thereof. These transition metal ions may form a salt or complex with inorganic anions or organic complexing ligands. Illustrative inorganic ions may be those selected from the group consisting of F$^-$, Cl$^-$, Br$^-$, I$^-$, NO$_3^-$, ClO$_4^-$, SO$_4^-$, PO$_4^-$, H$_2$O, O$_2^-$, OH$^-$, HO$_2^-$, SH$^-$, S$_2^-$, N$_3^-$, SCN$^-$, NH$_2^-$ and combinations thereof. Illustrative organic complexing ligands with which the transition metal may complex include those selected from the group consisting of RCOO$^-$, PR$_3$ or NR$_3$, where R is H, C$_1$–C$_{20}$ alkyl or aryl (optionally substituted), hexamethylphosphoric triamide, ethylenediamine, trimethylamine, bispyridylamine, pyridine, pyridazine, pyrimidine, pyrazine, imidazole, pyrazole and triazole rings. Other suitable ligands in their simplest forms are:

(i)
1,4,7-triazacyclononane;
1,4,7-triazacyclodecane;
1,4,7-trimethyl-1,4,7-triazacyclononane;
1,4,7-trimethyl-1,4,7-triazacyclodecane;
1,4,8-trimethyl-1,4,8-triazacycloundecane;
1,5,9-trimethyl-1,5,9-triazacyclododecane;
1,4-dimethyl-7-ethyl- 1,4,7-triazacyclononane;

(ii)
tris(pyridin-2-yl)methane;
tris(pyrazol-1-yl)methane;
tris(imidazol-2-yl)methane;
tris(triazol-1-yl)methane;

(iii)
tris(pyridin-2-yl)borate;
tris(triazol)-1-yl)borate;
tris(imidazol-2-yl)phosphine;
tris(imidazol-2-yl)borate;

(iv)
cis-cis-1,3,5-trisamino-cyclohexane;
1,1,1-tris(methylamino)ethane;

(v)
bis(pyridin-2-yl-methyl)amine;
bis(pyrazol-1-yl-methyl)amine;
bis(triazol-1-yl-methyl)amine;
bis(imidazol-2-yl-methyl)amine.

These ligands may be substituted on the amine nitrogen atoms and/or CH$_2$ carbon atoms and/or aromatic rings.

Amounts of the transition metal catalyst may range from 0.001 to 10%, preferably from 0.001 to 5%, optimally from 0.01 to 1% by weight.

Bleach systems of the present invention may be employed for a wide variety of purposes, but are especially useful in the cleaning of laundry. When intended for such purpose, the peroxygen compound and oxygen transfer agent of the present invention will usually also be combined with surface-active materials, detergency builders and other known ingredients of laundry detergent formulations.

The surface-active material may be naturally derived, or synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch. The total level of the surface-active material may range up to 50% by weight, preferably being from 0.5 to 40% by weight of the composition, most preferably 4 to 25%.

Synthetic anionic surface-actives are usually water-soluble alkali metal salts of organic sulphates and sulphonates having alkyl radicals containing from about 8 to about 22 carbon atoms.

Examples of suitable synthetic anionic detergent compounds are sodium and ammonium alkyl sulphates, especially those obtained by sulphating higher (C$_8$–C$_{18}$) alcohols produced for example from tallow or coconut oil; sodium and ammonium alkyl (C$_9$–C$_{20}$) benzene sulphonates, sodium alkyl glyceryl ether sulphates, especially those ethers of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher (C$_9$–C$_{18}$) fatty alcohol-alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; alkane monosulphonates such as those derived by reacting alpha-olefins ($C_8$–$C_{20}$) with sodium bisulphite and those derived by reacting paraffins with $SO_2$ and $Cl_2$ and then hydrolyzing with a base to produce a random sulphonate; sodium and ammonium $C_7$–$C_{12}$ dialkyl sulfosuccinates; and olefin sulphonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulphonates, sodium ($C_{16}$–$C_{18}$) alkyl sulphates and sodium ($C_{16}$–$C_{18}$) alkyl ether sulphates.

Examples of suitable nonionic surface-active compounds which may be used, preferably together with the anionic surface-active compounds, include in particular the reaction products of alkylene oxides, usually ethylene oxide, with alkyl ($C_6$–$C_{22}$) phenols, generally 5–25 EO, i.e. 5–25 units of ethylene oxide per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglucosides, long chain tertiary amine oxides, and fatty amido polyols such as methyl glucamines.

Amphoteric or zwitterionic surface-active compounds such as alkylamidopropyl betaines can also be used in the compositions of the invention. If any amphoteric or zwitterionic detergent compounds are used, it is generally in small amounts in compositions based on the much more commonly used synthetic anionic and nonionic actives.

Soaps may also be incorporated into the compositions of the invention, preferably at a level of less than 30% by weight. They are particularly useful at low levels in binary (soap/anionic) or ternary mixtures together with nonionic or mixed synthetic anionic and nonionic compounds. Soaps which are used are preferably the sodium, or less desirably potassium, salts of saturated or unsaturated $C_{10}$–$C_{24}$ fatty acids or mixtures thereof. The amount of such soaps can be varied between 0.5 and 25% by weight, with lower amounts of 0.5 to 5% being generally sufficient for lather control. Amounts of soap between 2 and 20%, especially between 5 and 15, are used to give a beneficial effect on detergency. This is particularly valuable in compositions used in hard water where the soap acts as a supplementary builder.

The detergent compositions of the invention will normally also contain a detergency builder. Builder materials may be selected from (1) calcium sequestrant materials, (2) precipitating materials, (3) calcium ion-exchange materials and (4) mixtures thereof.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethylmalonate, carboxymethyloxysuccinate, tartrate mono- and disuccinate, oxydisuccinate, crystalline or amorphous aluminosilicates and mixtures thereof.

Polycarboxylic homo- and co-polymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of, for example, from 1 to 80% by weight, preferably from 10 to 60% by weight.

Upon dispersal in a wash water, the initial amount of peroxygen compound should range anywhere from 0.05 to 250 ppm active oxygen per liter of water, preferably from 1 to 50 ppm. Within the wash media the amount of oxygen transfer agent initially present should be from 0.01 to 300 ppm, preferably from 5 to 100 ppm. Surfactant should be present in the wash water from 0.05 to 1.0 grams per liter, preferably from 0.15 to 0.20 grams per liter. When present, the builder amount will range from 0.1 to 3.0 grams per liter.

Apart from the components already mentioned, the detergent compositions of the invention can contain any of the conventional additives in the amounts in which such materials are normally employed in detergent compositions. Examples of these additives include dye transfer inhibition agents such as polyamine N-oxide polymers, metallo phthalocyanines, and polymers based on N-vinylpyrrolidone and N-vinylimidazole, lather boosters such as alkanolamides, particularly the monoethanolamides derived from palmkernel fatty acids and coconut fatty acids, lather-depressants such as alkyl phosphates and silicones, anti-redeposition agents such as sodium carboxymethylcellulose and alkyl or substituted alkylcellulose ethers, stabilizers such as ethylene diamine tetraacetic acid and phosphonic acid derivatives (Dequest®), fabric softening agents, inorganic salts such as sodium sulphate, and, usually present in very small amounts, fluorescent agents, perfumes, enzymes such as proteases, cellulases, lipases and amylases, germicides and colorants.

The oxygen transfer agents in combination with a peroxygen compound may be useful for removing stains both in consumer type products consumer products and for industrial applications. Among consumer products incorporating this invention are laundry detergents, laundry bleaches, hard surface cleaners, toilet bowl cleaners, automatic dishwashing compositions and even denture cleaners. Stained consumer products benefiting from treatment with compositions of this invention may include clothes and other fabrics; household fixtures and applicants such as sinks, toilet bowls and oven ranges; tableware such as drinking glasses, dishes, cookware and utensils; and even dentures. Hair colorants may also be formulated with the bleach composition of this invention. The bleaching system of this invention may also be applied to industrial uses such as for the bleaching of wood pulp.

The system of the present invention may be delivered in a variety of product forms including powders, on sheets or other substrates, in pouches, in tablets, in aqueous liquids, or in nonaqueous liquids such as liquid nonionic detergents.

The following examples will more fully illustrate the embodiments of this invention. All parts, percentages and proportions referred to herein and in the appended claims are by weight unless otherwise illustrated.

Examples 1–3 were prepared according to the procedure described by J. B. Wright in *J. Org. Chem* (1964), 29, 1905–1909.

EXAMPLE 1

Preparation of 3,4-diphenyl-1,2,5-thiadiazole-1,1-dioxide (Diphenyl Thiadiazole or DPT)

Benzil (10 g, 48 mmol) and sulfamide (4.6 g, 48 mmol) were combined in anhydrous, denatured ethanol (100 mL) and dry hydrogen chloride gas was bubbled into the reaction mixture until the temperature reached 55° C. The mixture was heated at reflux for 2 hrs, allowed to equilibrate and proceed overnight at room temperature. Concentration of the mixture gave a light yellow solid which was triturated first with water then with ether yielding 10.74 g (83%) of a white solid. The solids may be recrystallized if necessary from acetone to give white crystals.

mp: 240°–244° C. (lit. 248°–250° C.). GC-MS: m/z=271 $(M+H)^+$, 103 (PhC≡N). $^{13}C$ NMR (50 MHz, $CD_3CN$) δ 129.2, 129.5, 132.1, 134.8, 168.4(C=N).

EXAMPLE 2

Preparation of 3-methyl-4-phenyl-1,2,5-thiadiazole-1,1-dioxide (Methyl Phenyl Thiadiazole or MPT)

1-Phenyl-1,2-propanedione (12 g, 81 mmol) and sulfamide (7.8 g, 81 mmol) were combined in anhydrous, denatured ethanol (84 mL) and dry HCl gas was bubbled into the reaction mixture until the temperature reached 50° C. The mixture was heated at reflux for 3 hours and then allowed to proceed overnight at room temperature. Filtration of the mixture gave 0.55 g of a reddish solid which was discarded. The filtrate was concentrated to a yellow solid which was triturated with water and then ether affording 13.76 g (82 %) of a beige solid. The solid may be recrystallized from toluene to give beige colored crystals.

mp: 130°131° C. $^1$H NMR (200 MHz, CDCl$_3$) δ 2.77, 7.56–7.93 (m, Ar). $^{13}$C NMR (50 MHz, CDCl$_3$) δ 18.8 (CH$_3$), 127.3, 129.4, 130.2, 134.2, 165.8 (C=N), 167.9 (C=N). Cl-MS (NH$_3$): (M+H)$^+$209, (M+NH$_4$)$^+$226

EXAMPLE 3

Preparation of 3,4-dimethyl-1,2,5-thiadiazole-1,1-dioxide, (Dimethyl Thiadiazole or DMT)

2,3-Butanedione (12 g, 0.139 mol ) and sulfamide (13.44 g 0.139 mol) were combined in anhydrous, denatured ethanol (65 mL) and dry HCl gas was bubbled into reaction mixture until the temp. reached 60°–70° C. The mixture was heated to 70° C. for 2 hours. After cooling to room temp. a yellow precipitate formed which was diluted with boiling ethanol until a homogenous solution was obtained. The reaction mixture was set aside overnight at room temperature. Upon concentration, a brown solid was obtained which was triturated first with water and then with ether yielding 13.52 g (67%) of a beige colored solid. The solid may be recrystallized from isopropanol to give beige colored crystals.

mp: 143°–145° C. (lit. mp 149° C.) $^1$H NMR (200 MHz, CD$_3$CN) δ 2.50. $^{13}$C NMR (75 MHz, CD$_3$CN) δ 16.6 (CH$_3$), 172.2 (C=N). Cl-MS (NH$_3$): (M+H)$^+$147, (M+NH$_4$)$^+$164.

EXAMPLE 4

Tea Stain Bleaching Data Thiadiazole Dioxides

Bleaching studies were conducted by comparing the performance of representative bleaches with and without the presence of thiadiazole dioxides. In this regard, the stain removal observed without the intervention of thiadiazoles served as an experimental blank and the amount of stain removal by the thiadiazoles containing system constituted activation of a given bleach.

Stain bleaching experiments were conducted in a Terg-O-Tometer in 1000 mL of milli-Q water. These experiments were run employing 0.01M NaHCO$_3$ buffer with the pH adjusted to the reported value with 1N NaOH solution. Four tea stained (BC-1) cloths (3"×3") were added to each Terg pot. Tests were conducted at 40° C. and 20° C., as respectively reported in Table I and II. PAP was employed as the peracid drive and dosed at 7.5 ppm a.o. level. First the peracid was added to the system followed by an appropriate amount of thiadiazole.

Stain bleaching was measured reflectometrically using a Colorgard System/05 Reflectometer. Bleaching was indicated by an increase in reflectance less the effect of oxidant alone, reported as ΔΔR.

TABLE I

Bleaching Data for the Different Catalysts at a Concentration of 6 × 10$^{-5}$M at 40° C. with PAP

| pH | DMT | MPT | DPT | SULF-D |
|----|-----|-----|-----|--------|
| 8  | 0.7 | 1.6 | −0.3 | 0.9 |
| 9  | 1.3 | 3.1 | −1.1 | —   |
| 10 | 3.7 | 2.9 | 1.6 | 5.4 |

TABLE II

Bleaching Data for the Different Catalysts at a Concentration of 6 × 10$^{-5}$M at 20° C. with PAP

| pH | DMT | MPT | DPT | SULF-D |
|----|-----|-----|-----|--------|
| 8  | 0.6 | 1.9 | −0.2 | 0.6 |
| 9  | 1.8 | 3.5 | −0.2 | —   |
| 10 | 3.4 | 4.1 | 0.3 | 1.9 |

Tables I and II utilize the sulfonylimine Sulf-D (3-methyl-1,2-benzisothiazole 1,1-dioxide for comparison purposes. Performance of the thiadiazoles steadily increased with increasing pH. DMT and MPT appeared not to be temperature sensitive. DPT performed better at higher pH and temperature.

TABLE III

Concentration Dependence of Thiadiazoles on Tea Stain Bleaching

| | ΔΔR | | |
|---|---|---|---|
| WT CATALYST (mg/L) | DMT | MPT | DPT |
| 1 | 2.2 | 2.2 | 0.4 |
| 3 | 2.9 | 2.9 | −0.1 |
| 5 | 3.5 | 4.7 | 0.9 |

Wash Conditions: 30° C., pH 9.5, 20 min wash, 2.1 g/L Detergent (24% LAS, 14.5% STPP), 4.42 × 10$^{-4}$M TAED, 2.1 × 10$^{-3}$M sodium perborate monohydrate.

Table III records the effect of a different oxygen source, tetraacetylethylenediamine (TAED) with sodium perborate which generates peracetic acid. An LAS surfactant containing detergent powder was used in place of the sodium bicarbonate buffer. Good cleaning performance was obtained from the thiadiazoles even at low concentrations.

TABLE IV

Tomato Stain Bleaching Data For The Different Catalysts at the Concentration Of 6 × 10$^{-5}$M at 40° C. 7.5 ppm a.o. TAED, 24 ppm a.o. Perborate, 1.1 g/L Ultra All

| | | ΔB* | |
|---|---|---|---|
| Peroxygen Source | Catalyst | 20° C. | 40° C. |
| TAED/Perborate | None   | 0.2  | 0.6  |
| TAED/Perborate | Sulf-D | 0.0  | −0.2 |
| TAED/Perborate | DMT    | 0.3  | 0.0  |
| TAED/Perborate | MPT    | 11.6 | 4.0  |
| TAED/Perborate | DPT    | 11.2 | 14.0 |
| Perborate      | SNOBS  | 12.4 | 10.2 |

*ΔB is the bleaching on a red-yellow scale. Stain removal due to detergent has been subtracted. The higher the number, the more stain removal.

Table IV demonstrates the effect on spaghetti sauce, a hydrophobic stain. SNOBS was included for comparison since it is known to be a good hydrophobic stain bleach. DPT and MPT performed extremely well at 20° C. and are comparable to SNOBS. MPT was somewhat less effective at 40° C. while DPT was still very good. The sulfonylimine, Sulf-D, gave no benefit on this stain at either temperature.

The foregoing description and Examples illustrate selected embodiments of the present invention. In light thereof, various modifications will be suggested to one skilled in the art all of which are within the spirit and purview of this invention.

What is claimed is:

1. A bleaching composition comprising:
   (i) from 1 to 60% by weight of a peroxygen compound; and
   (ii) from 0.01 to 10% of an oxygen transfer agent whose structure is:

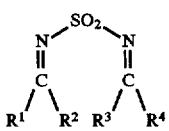

wherein:
R$^1$, R$^2$, R$^3$ and R$^4$ may each independently be hydrogen, nitro, halo or a C$_1$–C$_{40}$ substituted or unsubstituted radical selected from the group consisting of phenyl, aryl, acyl, heterocyclic ring, alkyl, cycloalkyl, cyano, alkoxy, keto, carboxylic and carboalkoxy radicals; and R$^2$ and R$^3$ may be absent and;
R$^1$ with R$^2$ or R$^2$ with R$^3$ or R$^3$ with R$^4$ or R$^1$ with R$^4$ may respectively independently form a ring system, and when R$^2$ and R$^3$ are absent, carbon atoms of the imine group may directly be bonded together to form a five, six or seven membered ring.

2. A composition according to claim 1 further comprising from 1 to 80% of a detergent builder.

3. A composition according to claim 1 further comprising from 0.5 to 50% of a surfactant.

4. A composition according to claim 1 further comprising an effective amount for cleaning of an enzyme selected from the group consisting of proteases, cellulases, lipases, amylases and mixtures thereof.

5. A composition according to claim 1 delivered in a form selected from the group consisting of a powder, sheet, pouch, tablet, aqueous liquid and nonaqueous liquid.

6. A composition according to claim 1 wherein the peroxygen compound is present in an amount from 1.5 to 25% and the oxygen transfer agent is present in an amount from 0.1 to 5% by weight.

7. A composition according to claim 1 wherein the peroxygen compound is an inorganic material selected from the group consisting of perborate, percarbonate, perphosphate, persilicate and monopersulphate salts.

8. A composition according to claim 1 wherein the peroxygen compound is an organic peroxyacid.

9. A composition according to claim 8 wherein the organic peroxyacid is selected from the group consisting of N,N-phthaloylaminoperoxycaproic acid, peracetic acid, monoperoxyphthalic acid and diperoxydodecanedioic acid.

10. A composition according to claim 1 wherein the peroxygen compound is a bleach precursor.

11. A method for bleaching a stained substrate, said method comprising contacting said stained substrate in an aqueous medium with a peroxygen compound, a surfactant in an effective amount to clean said substrate and with an oxygen transfer agent whose structure is:

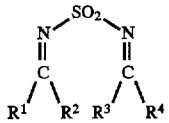

wherein:
R$^1$, R$^2$, R$^3$ and R$^4$ may each independently be hydrogen, nitro, halo or a C$_1$–C$_{40}$ substituted or unsubstituted radical selected from the group consisting of phenyl, aryl, acyl, heterocyclic ring, alkyl, cycloalkyl, cyano, alkoxy, keto, carboxylic and carboalkoxy radicals; and R$^2$ and R$^3$ may be absent and;
R$^1$ with R$^2$ or R$^2$ with R$^3$ or R$^3$ with R$^4$ or R$^1$ with R$^4$ may respectively independently form a ring system; and when R$^2$ and R$^3$ are absent, carbon atoms of the imine group may directly be bonded together to form a five, six or seven membered ring.

12. A method according to claim 11 wherein the ratio of peroxygen compound to oxygen transfer agent ranges from 100:1 to 1:1.

13. A method according to claim 11 wherein said substrate is selected from the group consisting of fabrics, household fixtures and tableware.

14. A method according to claim 11 wherein said substrate is a denture.

15. A method for bleaching a stained substrate, said method comprising contacting said stained substrate in an aqueous medium with a peroxygen compound and with an oxygen transfer agent whose structure is:

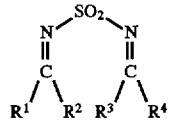

wherein:
R$^1$, R$^2$, R$^3$ and R$^4$ may each independently be hydrogen, nitro, halo or a C$_1$–C$_{40}$ substituted or unsubstituted radical selected from the group consisting of phenyl, aryl, acyl, heterocyclic ring, alkyl, cycloalkyl, cyano, alkoxy, keto, carboxylic and carboalkoxy radicals; and R$^2$ and R$^3$ may be absent and;
R$^1$ with R$^2$ or R$^2$ with R$^3$ or R$^3$ with R$^4$ or R$^1$ with R$^4$ may respectively independently form a ring system; and when R$^2$ and R$^3$ are absent, carbon atoms of the imine group may directly be bonded together to form a five, six or seven membered ring.

16. A method according to claim 15 wherein the oxygen transfer agent is present from about 5 ppm to about 100 ppm per liter of medium.

* * * * *